(12) United States Patent
Park et al.

(10) Patent No.: US 9,993,519 B2
(45) Date of Patent: Jun. 12, 2018

(54) ANTICANCER PEPTIDE FOR INHIBITING PROLIFERATION OF CANCER STEM CELLS AND USE THEREOF (71) Applicants: SEOUL NATIONAL UNIVERSITY R&DB FOUNDATION, Seoul (KR); NANO INTELLIGENT BIOMEDICAL ENGINEERING CORPORATION CO., LTD., Chungcheongbuk-do (KR)

(72) Inventors: Yoon Jeong Park, Seoul (KR); Chong-Pyoung Chung, Seoul (KR); Jue-Yeon Lee, Gyeonggi-do (KR); Jin Sook Suh, Seoul (KR)

(73) Assignees: SEOUL NATIONAL UNIVERSITY R&DB FOUNDATION, Seoul (KR); NANO INTELLIGENT BIOMEDICAL ENGINEERING CORPORATION CO., LTD., Chungcheongbuk-Do (KR)

( * ) Notice: Subject to any disclaimer, the term of this patent is extended or adjusted under 35 U.S.C. 154(b) by 0 days. days.

(21) Appl. No.: 15/113,823

(22) PCT Filed: Mar. 3, 2016

(86) PCT No.: PCT/KR2016/002109
§ 371 (c)(1),
(2) Date: Jul. 23, 2016

(87) PCT Pub. No.: WO2016/153185
PCT Pub. Date: Sep. 29, 2016

(65) Prior Publication Data
US 2017/0042963 A1 Feb. 16, 2017

(30) Foreign Application Priority Data
Mar. 26, 2015 (KR) ........................ 10-2015-0042700

(51) Int. Cl.
A61K 38/00 (2006.01)
A61P 35/00 (2006.01)
A61K 38/10 (2006.01)
A61K 9/00 (2006.01)
A61K 47/30 (2006.01)

(52) U.S. Cl.
CPC ................ *A61K 38/10* (2013.01); *A61K 9/00* (2013.01); *A61K 47/30* (2013.01)

(58) Field of Classification Search
CPC . A61K 38/00; A61K 31/145; A61K 2039/585
See application file for complete search history.

(56) References Cited

U.S. PATENT DOCUMENTS 5,595,756 A * 1/1997 Bally .................. A61K 9/1272
264/4.1
2015/0165060 A1* 6/2015 Park ........................ C07K 14/47
530/327

FOREIGN PATENT DOCUMENTS

EP 2700655 A1 2/2014
WO 0240512 A2 5/2002
WO 2010092571 A2 8/2010

OTHER PUBLICATIONS

Sporn et at, "Chemoprevention of Cancer," Carcinogenesis, vol. 21 (2000), 525-530.*
Auerbach et al, Cancer and Metastasis Reviews, 2000, 19: 167-172.*
Gura T, Science, 1997, 278(5340): 1041-1042, encloses 1-5.*
Jain RK, Scientific American, Jul. 1994,58-65.*
Cancer Drug Design and Discovery, Neidle, Stephen, ed. (Elsevier/Academic Press, 2008) p. 431.*
Aguiree-Ghiso, J., "Models, mechanisms and clinical evidence for cancer dormancy", "Nat Rev Cancer", Nov. 2007, pp. 834-846, vol. 7, No. 11.
Aradhya, S., et al., "NF-kappaB signaling and human disease", "Curr Opin Genet Dev.", Jun. 2001, pp. 300-306, vol. 11, No. 3.
Baccelli, I., et al., "The evolving concept of cancer and metastasis stem cells", "J. Cell. Biol.", Aug. 6, 2012, pp. 281-293, vol. 198, No. 3.
Barnes, P., et al., "Nuclear factor-kappaB: a pivotal transcription factor in chronic inflammatory diseases", "New England Journal of Medicine", Apr. 10, 1997, pp. 1066-1071, vol. 336, No. 15.
Campbell, K., et al., "Active repression of antiapoptotic gene expression by RelA(p65) NF-kappa B", "Molecular Cell", Mar. 26, 2004, pp. 853-865, vol. 13, No. 6.
Henkel, T., et al., "Intramolecular masking of the nuclear location signal and dimerization domain in the precursor for the p50 NF-kappa B subunit", "Cell", Mar. 20, 1982, pp. 1121-1133, vol. 68, No. 6.
Orlowski, R., et al., "NF-kappaB as a therapeutic target in cancer", "Trends in Molecular Medicine", Aug. 2002, pp. 385-389, vol. 8, No. 8.
Whiteside, A., et al., "I kappa B proteins: structure, function and regulation.", "Seminars in Cancer Biology", Apr. 1997, pp. 75-82, vol. 8, No. 2.
Xie, Q., et al., "Role of transcription factor NF-kappa B/Rel in induction of nitric oxide synthase", "Journal of Biological Chemistry", Feb. 18, 1994, pp. 4705-4708, vol. 269, No. 7.
Yamamoto, K., et al., "Transcriptional roles of nuclear factor kappa B and nuclear factor-interleukin-6 in the tumor necrosis factor alpha-dependent induction of cyclooxygenase-2 in MC3T3-E1 cells", "The Journal of Biological Chemistry", Dec. 29, 1995, pp. 31315-31320, vol. 270, No. 52.
Edited by Alfonso R. Gennaro, "Remington's Pharmaceutical Sciences", 1985, pp. 741-772; 1409-1677, Publisher: Mack Publishing Company.

(Continued)

Primary Examiner — Hasan S Ahmed
Assistant Examiner — Kaipeen E Yang
(74) Attorney, Agent, or Firm — Hultquist, PLLC; Steven J. Hultquist (57) ABSTRACT The present invention relates to an anticancer composition comprising a peptide that inhibits the proliferation of cancer stem cells present in tumor tissue and that induces apoptosis of such cancer stem cells, and more particularly, to an anticancer peptide that inhibits the activity of NF-κB which is overexpressed specifically in cancer stem cells present in tumors.

11 Claims, 5 Drawing Sheets (56) References Cited

OTHER PUBLICATIONS

Hruby, V. J., et al., "Designing Peptide Receptor Agonists and Antagonists", "Nature Reviews", Nov. 2002, pp. 847-858, vol. 1.
Lee, J. Y., et al., "Identification of a cell-penetrating peptide domain from human beta-defensin 3 and characterization of its anti-inflammatory activity", "International Journal of Nanomedicine", 2015, pp. 5423-5434, vol. 10.
Phan, T. K., et al., "Human b-defensin 3 contains an oncolytic motif that binds PI(4,5)P2 to mediate tumour cell permeabilisation", "Oncotarget", Dec. 9, 2015, pp. 2054-2069, vol. 7, No. 2.
Shuyi, Y., et al., "Human beta-defensin-3 (hBD-3) upregulated by LPS via epidermal growth factor receptor (EGFR) signaling pathways to enhance lymphatic invasion of oral squamous cell carcinoma", "Oral Surgery, Oral Medicine, Oral Pathology, Oral Radiology and Endodontics", Nov. 2011, pp. 616-625, vol. 112, No. 5.
Uraki, S., et al., "Human b-defensin-3 inhibits migration of colon cancer cells via downregulation of metastasis-associated 1 family, member 2 expression", "International Journal of Oncology", 2014, pp. 1059-1064, vol. 45.
Wang, K., et al., "Effect of human beta-defensin-3 on head and neck cancer cell migration using micro-fabricated cell islands", "Head & Neck Oncology", 2012, pp. 41-48, vol. 4.
Xu, D., et al., "Human beta-defensin 3 contributes to the carcinogenesis of cervical cancer via activation of NF-kB signaling", "Oncotarget", Oct. 4, 2016, pp. 75902-75913, vol. 7, No. 46.
Note: For the non-patent literature citations that no month of publication is indicated, the year of publication is more than 1 year prior to the effective filing date of the present application.

\* cited by examiner

FIG. 1

| Phosphorylation site | Unphospho-form ratio | Phospho-form ratio | Phosphorylation ratio |
|---|---|---|---|
| NF-κB-p65 (Phospho-Ser536) | 1.003095525 | 3.183445355 | 3.173621332 |
| FER (Phospho-Tyr402) | 0.752486793 | 2.17325882 | 2.888094603 |
| 14-3-3 theta/tau (Phospho-Ser232) | 0.998098774 | 2.354112086 | 2.35859629 |
| c-Jun (Phospho-Thr93) | 0.648592839 | 1.524220897 | 2.350042748 |
| MEK1 (Phospho-Thr386) | 0.885167283 | 1.865870941 | 2.107383677 |
| HSL (Phospho-Ser554) | 0.60481566 | 1.219610098 | 2.016486874 |
| Cyclin D1 (Phospho-Thr288) | 1.071960689 | 2.074133852 | 1.934897309 |
| p44/42 MAP Kinase (Phospho-Thr202) | 0.933178517 | 1.728534022 | 1.852307989 |
| B-RAF (Phospho-Thr598) | 0.589540569 | 1.086527282 | 1.843006808 |
| STAT5A (Phospho-Ser780) | 0.750825346 | 1.328368116 | 1.769917728 |
| PDGF R beta (Phospho-Tyr1021) | 0.680069926 | 1.194955568 | 1.757106942 |
| 14-3-3 zeta (Phospho-Ser58) | 0.846025703 | 1.468103418 | 1.735294108 |
| P38 MAPK (Phospho-Thr180) | 0.69856361 | 1.212098052 | 1.735080862 |

Higher value of phosphorylation ratio between CD44$^{low}$ cells vs. CD44$^{high}$ cells meant higher phosphorylation state in CD44$^{high}$ cells compared to CD44$^{low}$ cells.

```
                        SEQUENCE LISTING

<160> NUMBER OF SEQ ID NOS: 3

<210> SEQ ID NO 1
<211> LENGTH: 15
<212> TYPE: PRT
<213> ORGANISM: Artificial Sequence
<220> FEATURE:
<223> OTHER INFORMATION: BD3-3

<400> SEQUENCE: 1

Gly Lys Cys Ser Thr Arg Gly Arg Lys Cys Cys Arg Arg Lys Lys
1               5                   10                  15

<210> SEQ ID NO 2
<211> LENGTH: 15
<212> TYPE: PRT
<213> ORGANISM: Artificial Sequence
<220> FEATURE:
<223> OTHER INFORMATION: BD3-3M1

<400> SEQUENCE: 2

Gly Lys Cys Ser Thr Arg Gly Arg Lys Cys Met Arg Arg Lys Lys
1               5                   10                  15

<210> SEQ ID NO 3
<211> LENGTH: 15
<212> TYPE: PRT
<213> ORGANISM: Artificial Sequence
<220> FEATURE:
<223> OTHER INFORMATION: BD3-3M2

<400> SEQUENCE: 3

Gly Lys Cys Ser Thr Arg Gly Arg Lys Met Cys Arg Arg Lys Lys
1               5                   10                  15
```

ANTICANCER PEPTIDE FOR INHIBITING PROLIFERATION OF CANCER STEM CELLS AND USE THEREOF

CROSS-REFERENCE TO RELATED APPLICATIONS

This application is a U.S. national phase under the provisions of 35 U.S.C. § 371 of International Patent Application No. PCT/KR16/02109 filed Mar. 3, 2016, which in turn claims the benefit of Korean Patent Application No. 10-2015-0042700 filed Mar. 26, 2015. The disclosures of such international patent application and Korean priority patent application are hereby incorporated herein by reference in their respective entireties, for all purposes.

TECHNICAL FIELD

The present invention relates to an anticancer composition comprising a peptide that inhibits the proliferation of cancer stem cells present in tumor tissue and that induces apoptosis of such cancer stem cells, and more particularly, to an anticancer peptide that inhibits the activity of NF-κB which is overexpressed specifically in cancer stem cells present in tumors.

BACKGROUND ART

The presence of cancer stem cells was suggested by the hypothesis that the proliferation of tumors is maintained by some cells having high malignancy among tumor cells. In fact, cancer stem cells have been isolated from blood cancers and solid cancers. Such cancer stem cells can generally form tumors, can induce the metastasis of tumors in vivo, and can create other types of cancer stem cells capable of differentiating into cells having various characters (Baccelli I et al., J Cell Biol 198:281-293, 2012). Thus, these cancer stem cells have outstanding characteristics in that they divide asymmetrically and have the ability to self-renew and proliferate to form tumors.

According to reports to date, it is a common theory that, due to the abilities of cancer stem cells to divide and metastasize, tumors cannot be removed only by induction of apoptosis of general cancer cells present in the tumors. Cancer stem cells in tumors are supported by microenvironments (niches) that can maintain the characteristics of these cells, and such environments including various immune cells, stromal cells, cancer cells and extracellular matrix may impart the characteristics of cancer stem cells to cells other than cancer stem cells. However, cancer stem cells remain in the resting state, unlike other cancer cells, and are less aggressive than metastatic cancer cells. Thus, cancer stem cells overcome the challenge of anticancer agents, and if a number of cancer stem cells present in tumors are activated due to external attack of inflammation or toxic substances, these cells are able to enter the cell cycle at high speed to thereby have the ability to proliferate (Wilson A et al., Nat Rev Cancer 7:834-346, 2007).

In preliminary experiments for the present invention, it was found that, when a cell population with high expression of CD44 that is one of cancer stem cells markers was isolated from metastasized breast cancer cells and subjected to a phosphorylation assay, the most highly phosphorylated protein was nuclear factor kappa B (hereinafter referred to as "NF-κB"). In fact, it is known that NF-κB is involved in the proliferation of cells and activated in cancer cells and cancer stem cells.

Generally, NF-κB of a p50/p65 in the resting state binds to IκB-α and exists in the cytoplasm in an inactive state (Simon, T. W. et al., Semin. Cancer Biol. 8:75-82, 1997). Because IκB-α bound to NF-κB masks the nuclear localization sequence (NLS) of NF-κB and IκB-α contains a strong nuclear export sequence (NES), NF-κB remains in the cytoplasm without moving to the nucleus (Thomas, H. et al., Cell. 68:1121-1133, 1992). If various intracellular and extracellular signals and stress are applied to cells, the degradation of IκB-α by protease due to its phosphorylation and ubiquitination will occur, and for this reason, the NLS of NF-κB masked by binding to IκB will be unmasked, whereby NF-κB remaining in the cytoplasm will be liberated, will rapidly move fast to the nucleus, and will bind to its target gene to activate the transcription of the gene.

It has been reported that the intracellular activation of NF-κB regulates the transcriptional activity of not only genes such as not only inflammation-related enzymes (cyclooxygenase II (COX-2), and inducible nitric oxide synthase (iNOS)), stress-response proteins, receptors (interleukin-2-receptor, and T-cell receptor), cytokines (interleukin-1, -2, -6 and -12, and TNF-α), and chemokines (interleukin-8), which are involved in inflammatory reactions, but also genes such as cyclin D1, TRAF1 (tumor necrosis factor-receptor associated factor 1), and c-IAP (inhibitor of apoptosis) 1, which are involved in apoptosis and cell proliferation (Barnes, P et al., Engl. J. Med. 366:1066-1071, 1997; Xie, Q et al., J. Biol. Chem. 269:4705-4708, 1994; Yamamoto, K. et al., J. Biol. Chem. 270:31315-31320, 1995).

In particular, it was found that abnormal NF-κB activation regulates various genes that are involved not only in inflammation-related diseases, but also in cell carcinogenesis, proliferation, invasion and angiogenesis (Aradhya, S. et al., Curr. Opin. Genet. Dev., 11:300-7, 2001; Orlowski, R. Z. et al., Trnds Mol. Med., 8:385-9, 2002). In addition, it has been reported that abnormal NF-κB activation plays an important role in malignancy of cancer cells. Furthermore, it is known that NF-κB confers drug resistance to cancer cells treated with anticancer agents and induces the expression of genes that promotes the survival of the cancer cells (Campbell K J et al., Mol Cell 13:853-865, 2004). As described above, it is expected that regulating the activity of NF-κB not only inhibits the growth of cancer stem cells, but also is involved in the signaling mechanism of cancer cells in microenvironments in which cancer stem cells exist, thereby exhibiting the effect of inhibiting tumor proliferation.

Accordingly, the present inventors have made extensive efforts to develop an effective anticancer therapeutic drug that inhibits the proliferation of cancer cells and cancer stem cells and that induces apoptosis of such cells. As a result, the present inventors have discovered and synthesized a functional peptide from an organic material present in vivo, and have found that, when breast cancer stem cells are treated with the peptide, the peptide exhibits the effect of inhibiting NF-κB activity to inhibit the proliferation of the cells and induce apoptosis of the cells, thereby preventing the present invention.

DISCLOSURE OF INVENTION

It is an object of the present invention to provide a use of a peptide representing growth inhibition and apoptotic effects of cancer stem cells.

To achieve the above object, the present invention provides an anticancer composition containing, as an active ingredient, a peptide represented by an amino acid sequence of the following formula I:

GKCSTRGRKX¹X²RRKK  [Formula I]

wherein $X^1$ and $X^2$ are each cysteine (C) or methionine (M).

The present invention also provides a method for treating cancer, which comprises administering the anticancer composition containing, as an active ingredient, a peptide represented by an amino acid sequence of the above formula I.

The present invention also provides a use of the peptide represented by an amino acid sequence of the above formula I for treating cancer.

BEST MODE FOR CARRYING OUT THE INVENTION

Unless defined otherwise, all technical and scientific terms used herein have the same meaning as commonly understood by one of ordinary skill in the art to which the invention pertains. Generally, the nomenclature used herein and the experiment methods, which will be described below, are those well-known and commonly employed in the art.

In the present invention, a functional peptide was discovered from an organic material present in vivo, and breast cancer stem cells were treated with the peptide. As a result, it was found that the peptide inhibited the intranuclear movement of NF-κB protein to inhibit NF-κB signaling, indicating that the peptide exhibits anticancer therapeutic effects by inhibition of proliferation of cancer cells and induction of apoptosis of such cells.

Thus, in one aspect, the present invention is directed to an anticancer composition containing, as an active ingredient, a peptide represented by an amino acid sequence of the following formula I:

GKCSTRGRKX¹X²RRKK  [Formula I]

wherein $X^1$ and $X^2$ are each cysteine (C) or methionine (M).

In the present invention, the peptide preferably comprises any one selected from the group consisting of SEQ ID NOs: 1 to 3, and more preferably comprises SEQ ID NOs: 1.

In the present invention, the peptide may inhibit the intranuclear movement of NF-κB protein in cancer cells or cancer stem cells to thereby inhibit NF-κB activity.

In the present invention, the peptide may inhibit proliferation of cancer cells or cancer stem cells and induce apoptosis of such cells.

In the present invention, the cancer stem cells are preferably those included in cancer cells derived from a metastatic tumor. Herein, the metastatic tumor has the same meaning as cancer.

In the present invention, the metastatic tumor is preferably selected from the group consisting of uterine cervical cancer, blood cancer, lung cancer, pancreatic cancer, non-small cell lung cancer, liver cancer, colon cancer, bone cancer, skin cancer, head or neck cancer, skin melanoma, intraocular melanoma, uterine cancer, ovarian cancer, rectal cancer, stomach cancer, anal cancer, breast cancer, fallopian tube carcinoma, endometrial carcinoma, vaginal cancer, vulva carcinoma, Hodgkin's disease, esophageal cancer, small intestine cancer, endocrine cancer, thyroid cancer, parathyroid cancer, adrenal cancer, soft tissue sarcoma, urethral cancer, penis cancer, prostate cancer, kidney cancer, and ureter cancer, but is not limited thereto.

As used herein, the term "composition" is intended to include not only a product containing a specific component but also any product made directly or indirectly by the combination of a specific component.

In the present invention, the composition may further comprise a pharmaceutically acceptable carrier. The carrier pharmaceutically acceptable may be at least one selected from the group consisting of physiological saline, sterile water, Ringer's solution, buffered saline, dextrose solution, maltodextrin solution, glycerol, and ethanol, but is not limited thereto.

In the present invention, the composition may further contain at least one additive selected from the group consisting of an excipient, a buffer, an antimicrobial preservative, a surfactant, an antioxidant, a tonicity adjuster, a preservative, a thickener, and a viscosity modifier, but is not limited thereto.

In the present invention, the pharmaceutical composition may be formulated for oral administration, for injection administration, or in the form of a gelling agent for local transplantation, but is not limited thereto. The composition of the present invention may be prepared into a suitable formulation using a known technique (Joseph Price Remington, *Remington's Pharmaceutical Science,* 17th edition, Mack Publishing Company, Easton Pa.).

The cancer stem cell proliferation inhibitor or anticancer composition according to the present invention can be administered through routes that are usually used in the medical field. The composition of the present invention is preferably administered parenterally. The composition according to the present invention may be administered, for example, orally, intravenously, intramuscularly, intraarterially, intramedullarily, intradually, intracardially, transdermally, subcutaneously, intraperitoneally, intrarectally, sublingually or topically.

In the present invention, the gelling agent for local transplantation comprises a synthetic polymer such as polylacticglycolic acid, poloxamer or propylene glycol, or a natural polymer such as collagen, alginic acid, propylene glycol alginic acid, chondroitin sulfate or chitosan, but is not limited to thereto.

The dose of the cancer stem cell proliferation inhibitor or anticancer composition according to the present invention may vary depending on the patient's weight, age, sex, health condition and diet, the time of administration, the mode of administration, excretion rate, the severity of the disease, or the like, and can be easily determined by those skilled in the art in consideration of the above factors.

The composition of the present invention may be administered as an individual therapeutic agent or in combination with other therapeutic agents, and may be administered sequentially or simultaneously with conventional therapeutic agents. Furthermore, the composition of the present invention may be used simultaneously with other therapeutic method such as radiation therapy.

The present invention is directed to a method for treating cancer comprising a step of administering an anticancer composition containing, as an active ingredient, a peptide represented by an amino acid sequence of the following formula I:

GKCSTRGRKX$^1$X$^2$RRKK   [Formula I]

wherein X$^1$ and X$^2$ are each cysteine (C) or methionine (M).

The present invention is directed to the use of an anticancer composition containing, as an active ingredient, a peptide represented by an amino acid sequence of the following formula I, for the treatment of cancer:

GKCSTRGRKX$^1$X$^2$RRKK   [Formula I]

wherein X$^1$ and X$^2$ are each cysteine (C) or methionine (M).

As used herein, the term "tumor" refers to a cyst in an organ or a parenchymal cell population in blood, which is formed by cancer cell or cancer stem cell populations and proliferate abnormally. The term "metastatic tumor" has the same meaning as "cancer".

In the present invention, the term "cancer cells" is meant to include cells that grow abnormally due to genetic modification in the proliferation and growth mechanisms of normal cells and that have the capability to aggressively move to other organs, which can be designated as metastasis.

In the present invention, "cancer stem cells" are known to be present in tumors, and are believed to occur due to abnormal metastasis of the genetic information of normal stem cells. It is known that cancer stem cells are maintained and proliferated due to the presence of microenvironments (niches) for their survival, and that normal cells, immune-related cells or differentiated cancer cells, which are present around cancer stem cells, influence the maintenance of characteristics and proliferation of these cancer stem cells.

EXAMPLES

Hereinafter, the present invention will be described in further detail with reference to examples. It will be obvious to a person having ordinary skill in the art that these examples are illustrative purposes only and are not to be construed to limit the scope of the present invention. Thus, the substantial scope of the present invention will be defined by the appended claims and equivalents thereof.

Example 1: Analysis of Phosphorylation Antibody Array of Cancer Stem Cells

In order to find activated proteins abnormally overexpressed in cancer stem cells, cancer stem cells were isolated from metastasized breast cancer cells. Specifically, a cell population with overexpression of CD44 known as a cancer stem cell marker protein was isolated by FACS Aria and was named "CD44$^{high}$ cells". On the contrary, a cell population with very low expression of CD44 was named "CD44$^{low}$ cells". The phosphorylation pattern of CD44 in CD44$^{high}$ cells similar to cancer stem cells was analyzed comparatively with that in CD44$^{low}$ cells.

Comparative analysis of the phosphorylation pattern was performed using a phospho explorer antibody microarray and an assay kit purchased from Full Moon Biosystems (USA). The cells isolated by FACS Aria according to CD44 expression levels were lysed, and the phospho explorer antibody microarray of the lysed cell solutions using the purchased kit was performed by E-Biogen Inc. (Korea).

Figure 1:
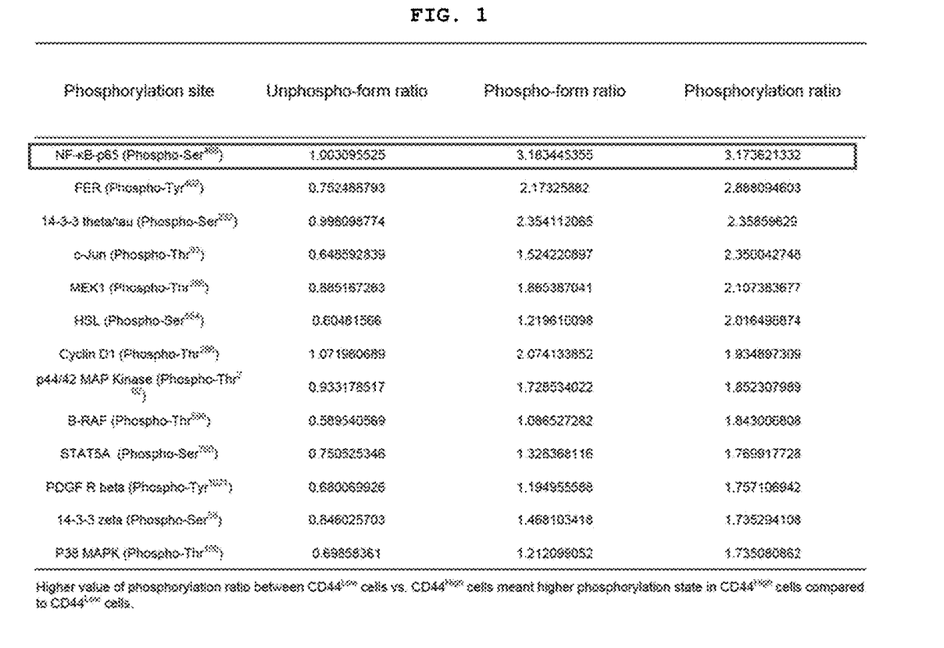
FIG. 1 shows the results of isolating and collecting cell populations according to the expression level of CD44 in metastasized breast cancer cells (MDA-MB-231) and performing a phosphorylation assay to discover a protein phosphorylated to increase its activity.

As a result, as shown in FIG. 1, when the results of quantitative analysis of phosphorylated proteins were arranged in a descending order by dividing the value of CD44$^{high}$ cells by the value of CD44$^{low}$ cells, it can be seen that phosphorylation of NF-κB-p65 at the S468 site occurred at the highest ratio. In addition, protein candidates activated in the CD44$^{high}$ population of the metastatic breast cancer cells that can be regarded as cancer stem cells are shown in FIG. 1, and these protein candidates have a potential as a specific marker of cancer stem cells. In particular, the most highly activated NF-κB is consistent with the report that NF-κB is abnormally activated in cancer stem cells. Thus, the present inventors have selected NF-κB as a target protein for the cancer stem cell line or the CD44$^{high}$ cancer cell population, and have developed a peptide that inhibits the activity of NF-κB protein.

Example 2: Synthesis of Peptide for Inhibiting Cancer Stem Cell Proliferation

A peptide of the following SEQ ID NO: 1 was synthesized starting from the C-terminus by an F-moc solid phase chemical synthesis method using a peptide synthesizer. Specifically, the peptide was synthesized using a Rink resin (0.075 mmol/g, 100-200 mesh, 1% DVB crosslinking) having bound thereto Fmoc-(9-fluorenylmethoxycarbonyl) as a blocking group. 50 mg of the Rink resin was placed in a synthesizer, after which the resin was swollen with DMF and treated with a 20% piperidine/DMF solution to remove the Fmoc-group. According to the sequence starting from the C-terminus, 0.5 M amino acid solution (solvent: DMF), 1.0 M DIPEA (solvent: DMF&NMP) and 0.5 M HBTU (solvent: DMF) were added to the resin in amounts of 5, 10 and 5 equivalents, respectively, and reacted under a nitrogen atmosphere for 1-2 hours. After completion of each of the deprotection and coupling steps, the resin was washed twice with each of DMF and NMP. Even after the last amino acid was coupled, deprotection was performed to the Fmoc-group.

The peptide synthesis was confirmed using the ninhydrin test method. After completion of the test, the synthesized resin was dried using THF or DCM, and then a TFA cleavage cocktail was added to the resin in an amount of 20 ml per g of the resin, followed by shaking for 3 hours. Next, a cocktail containing the resin and peptide dissolved therein was separated by filtration. After the filtered solution was removed using a rotary evaporator, cold ether was added or an excessive amount of cold ether was added directly to the TFA cocktail solution containing the peptide dissolved thereto to thereby crystallize the peptide into a solid, and the peptide was separated by centrifugation. The separated peptide was washed several times with ether and centrifuged to thereby completely remove the TFA cocktail. The resulting peptide was added to distilled water and freeze-dried.

```
SEQ ID NO: 1 (hBD3-3):
GKCSTRGRKCCRRKK
```

The synthesized peptide sequence was cleaved from the resin, washed, freeze-dried, and then purified by liquid chromatography. The molecular weight of the purified peptide was analyzed by mass spectrometry.

In the same manner as described above, a peptide of SEQ ID NO: 2 wherein the cysteine at position 5 in the C-terminus of the peptide of SEQ ID NO: 1 is substituted with methionine was synthesized by an F-moc solid chemical synthesis method using a peptide synthesizer.

```
SEQ ID NO: 2 (hBD3-3 M1):
GKCSTRGRKCMRRKK
```

The Subsequently, a peptide of SEQ ID NO: 3 wherein the cysteine at position 6 in the C-terminus of the peptide of SEQ ID NO: 1 is substituted with methionine was synthesized by an F-moc solid chemical synthesis method using a peptide synthesizer.

```
SEQ ID NO: 3 (hBD3-3 M2):
GKCSTRGRKMCRRKK
```

Example 3: Examination of Intracellular Permeability of Peptide for Inhibiting Cancer Stem Cell Proliferation 3-1: Synthesis of Fluorescent Dye for Peptide for Inhibiting Cancer Stem Cell Proliferation The peptides of SEQ ID NO: 1-3 synthesized in Example 2 were labeled with a fluorescent dye in order to their ability to permeate cells. 10 equivalents of rhodamine B was coupled to the N terminus of each of the synthesized peptides using triethylamine, and the molecular weight of each of the labeled peptides was analyzed by mass spectrometry to confirm the synthesis thereof.

Using reverse phase liquid chromatography, analysis and purification were performed. For analysis, 0.1% TFA/$H_2O$ and 0.092% TFA/acetonitrile were run through a $C_{18}$ column (diameter: 4.6 mm) with a gradient from 0 to 60% at a flow rate of 1 ml/min for 30 minutes. Herein, a UV detector was set at a wavelength of 220 nm. Purification was performed at a flow rate of 20 ml/min using a column (diameter: 2.2 cm) and the same solvents and detection wavelength as used in the analysis. Only pure peptides were collected, and the solvents were removed with a rotary evaporator, followed by freeze drying.

3-2: Fluorescence Imaging Measurement of Cellular Permeability of Peptide for Inhibiting Cancer Stem Cell Proliferation In order to measure the cellular permeability of the peptide for inhibition of cancer stem cell proliferation to thereby confirm the effective function thereof, hBCSCs (human Breast Cancer Stem cells, Celprogen, USA; positive for CD44) were seeded in a 4-well chamber slide at a density of $1 \times 10^4$ cells per well, and then cultured in hBCSC complete medium (Celprogen, USA) for 20 hours. 200 μM of each of the fluorescence-labeled peptides for inhibiting of cancer stem cell proliferation, obtained by coupling a fluorescent dye (Rhodamine B, SIGMA, USA) to the N-terminus of each of the peptides (SEQ ID NO: 1-3), and isolating and purifying the labeled peptides, was added to each well, and at 10 minutes after addition of the peptides, each well was washed twice with phosphate buffered saline (PBS), and then observed with a confocal scanning microscope (IX 70, Olympus Co., Tokyo, Japan).

Figure 2:
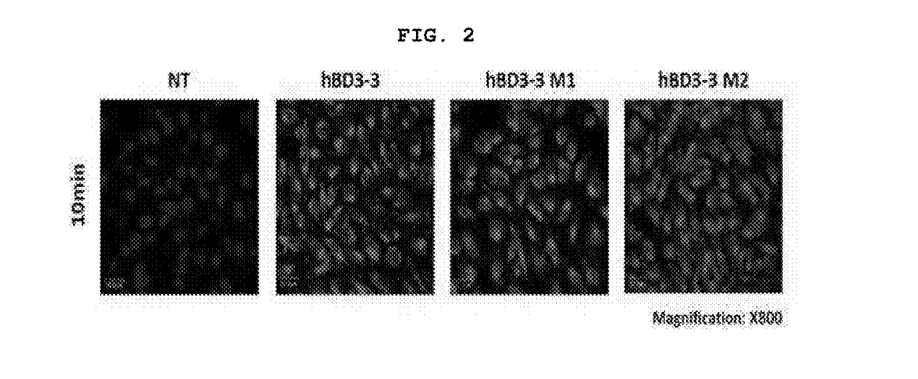
FIG. 2 shows the results of confocal laser scanning microscopic observation of the intracellular permeability of a cancer stem cell proliferation inhibitory peptide in breast cancer stem cells.

As a result, as shown in FIG. 2, when the cells were treated with each of the cancer stem cell proliferation inhibitory peptide, which were labeled with the fluorescent dye (rhodamine B, red), fluorescent particles were observed in the cells at 10 minutes after the treatment in all the cases treated with the cancer stem cell proliferation inhibitory peptides (SEQ ID NO: 1-3). This suggests that 50% or more of the cationic amino acids included in the cancer stem cell proliferation inhibitory peptide permeated the cells within a short time due to their specific gravity.

Example 4: Examination of the Effect of Cancer Stem Cell Proliferation Inhibitory Peptide on Inhibition of Self-Renewal 4-1: Examination of the Ability of Cancer Stem Cell Proliferation Inhibitory Peptide to Form Suspended Colonies In order to confirm the ability of the cancer stem cell proliferation inhibitory peptide to inhibit stem cell-like self-renewal, $1 \times 10^3$ hBCSCs were seeded in a 6-well plate, and then cultured in DMEM/F12 medium (Invitrogen, USA) containing B27 serum-free supplement (1:50; Invitrogen), 50 ng/mL hrEGF and hrbFGF (human recombinant epidermal growth factor and human recombinant basic fibroblast growth factor) (Peprotech, USA). The cells were treated with 0, 100 and 200 μM of each of the cancer stem cell proliferation inhibitory peptides (SEQ ID NO: 1-3) at 48-hour intervals after the cell seeding. 1 ml of medium was added once every 4 days, and a change in the size of suspended colonies formed was checked by continuous monitoring.

Figure 3:
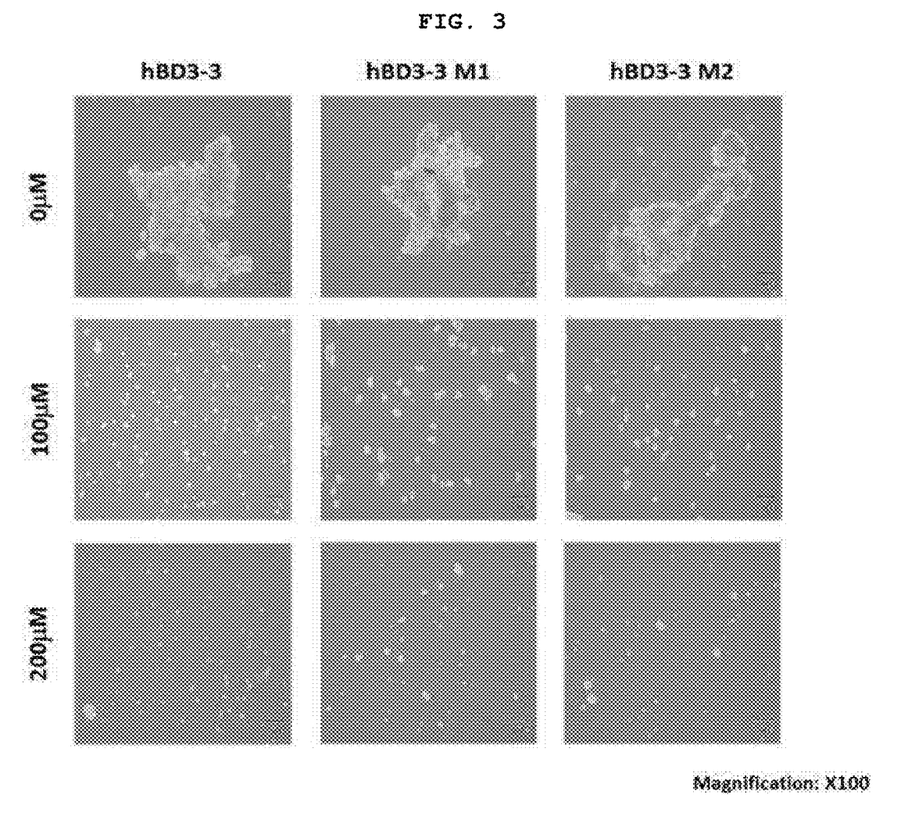
FIG. 3 shows the formation of suspended colonies (mammospheres) inhibited by a cancer stem cell proliferation inhibitory peptide in breast cancer stem cells.

As a result, as shown in FIG. 3, after 14 days of culture, the size of colonies produced did significantly differ between the group treated with the peptide and the group not treated with the peptide. In the group treated not with the peptide, the seeded cells formed colonies which were gathered together to form larger colonies, and thus suspended colonies having a diameter of about 100 μm or more were produced at the time point of observation. However, in the group treated with the peptide, very small colonies were formed at peptide concentrations of 100 and 200 μM, and the maximum diameters thereof did not exceed 20 μm or more. However, this pattern was clearly observed at a peptide concentration of 200 μM. In addition, it could be seen that the number of suspended cells was smaller than that of the peptide-treated group. These results indicate that treatment of cancer stem cells with the cancer stem cell proliferation inhibitory peptide inhibits the self-renewal ability of the cancer stem cells to thereby delay the production of colonies or to reduce the number of viable cells.

Figure 4:
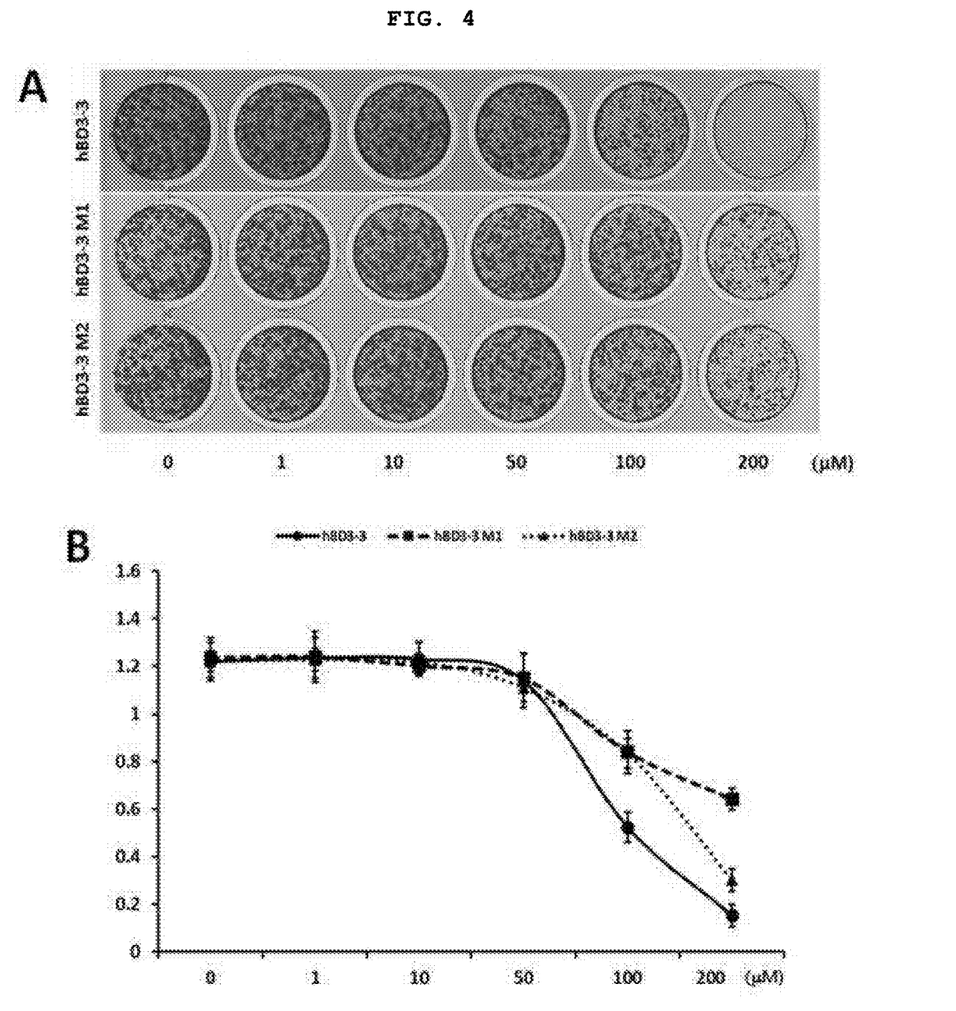
FIG. 4 shows the formation of adherent colonies inhibited by a cancer stem cell proliferation inhibitory peptide in breast cancer stem cells (A: images of stained colonies, and B: absorbance graph showing the formation of colonies).

4-2: Examination of the Ability of Cancer Stem Cell Proliferation Peptide to Form Adherent Colonies In order to confirm the ability of the cancer stem cell proliferation inhibitory peptide to inhibit stem cell-like self-renewal, unlike the method of observing the suspended colonies, cells were induced to grow under general culture conditions so that cellular changes occurring under stable conditions would be observed within a short time. $5 \times 10^2$ hBCSCs were seeded in each well of a 24-well plate, and then cultured in hBCSC complete medium (Celprogen, USA). After the cell seeding, the cells were treated with 0, 1, 10, 50, 100 and 200 μM of each of the cancer stem cell proliferation inhibitory peptides (SEQ ID NO: 1-3) at 48-hour intervals. The medium was replaced once every 3 days, and a change in colonies formed was checked by continuous monitoring. At 5 days after the start of culture, the cells were fixed using Carnoy's fixative (75% methanol and 25% acetic acid) at room temperature for 5 minutes, and the supernatant was removed, after which the cells were dried in air. The produced colonies were stained with 0.4% crystal violet for 5 minutes. After suction of the solution, the colonies were washed twice with distilled water and scanned. To evaluate the degree of staining of the confirmed colonies, the colonies were lysed by stirring with 10% acetic acid at room temperature for 10 minutes, and transferred to a 96-well plate, and the absorbance at 590 nm was measured. FIG. 4 shows the results (A: images of stained colonies, and B: absorbance graph showing the formation of colonies).

As a result, as shown in FIG. 4, a reduction in the production of colonies could be observed in the groups treated with 100 μM and 200 μM of the peptide. This reduction was concentration-dependent at a concentration of 100 μM or higher, but there was no difference in the degree of reduction between the peptide sequences. Such results are consistent with the results of Example 4-1, and thus show that proliferation of the cancer stem cells was inhibited by treatment with a certain concentration of the peptide independently of the difference between the environments in which the cells were suspended and adhered.

Example 5: Examination of the Effect of Cancer Stem Cell Proliferation Inhibitory Peptide on Apoptosis Whether the cell proliferation inhibitory effect of the cancer stem cell proliferation inhibitory peptide can ultimately induce apoptosis was analyzed by an annexin V/propidium iodide (PI) staining assay. The principle of the staining assay is as follows. In normal living cells, phosphatidyl serine (PS) is located in the cytoplasm. However, if cells enter the death phase through the apoptotic mechanism, PS is exposed to the outside of the cell membrane. At this time, annexin V binds to PS in the presence of calcium ions to emit light. Particularly, in the initial stage of apoptosis, PI staining the nucleus cannot pass through the cell membrane, and thus the cells are positive for annexin V staining and are negative for PI. However, if cells are positive for the two dyes, it can be seen that the cells underwent either the late state of apoptosis or necrosis.

To quantitatively analyze the degree of apoptosis, $5 \times 10^5$ hBCSCs were seeded in each well of a 6-well plate, and then cultured in hBCSC complete medium (Celprogen, USA). After 20 hours, the cells were treated with 0 and 200 μM of each of the cancer stem cell proliferation inhibitory peptides (SEQ ID NO: 1-3). After 8 hours, the cells were collected with medium by scraping with a cell scraper and centrifuged to remove the supernatant, and this process was repeated twice. A positive control group was treated with 50 μM of camptothecin instead of the peptide. 1× annexin V and 100 ng PI were dissolved in 1× annexin-binding buffer (10 mM HEPES, 140 mM NaCl, 2.5 mM $CaCl_2$, pH 7.4) and added to each of the cell groups to a total volume of 100 μL. After treatment at room temperature for 15 minutes, the size of the cells and the change in the cell population by treatment with the peptide were observed at FL-1/2 (488 nm and 585 nm) using FACSCalibur (BD, USA).

Figure 5:
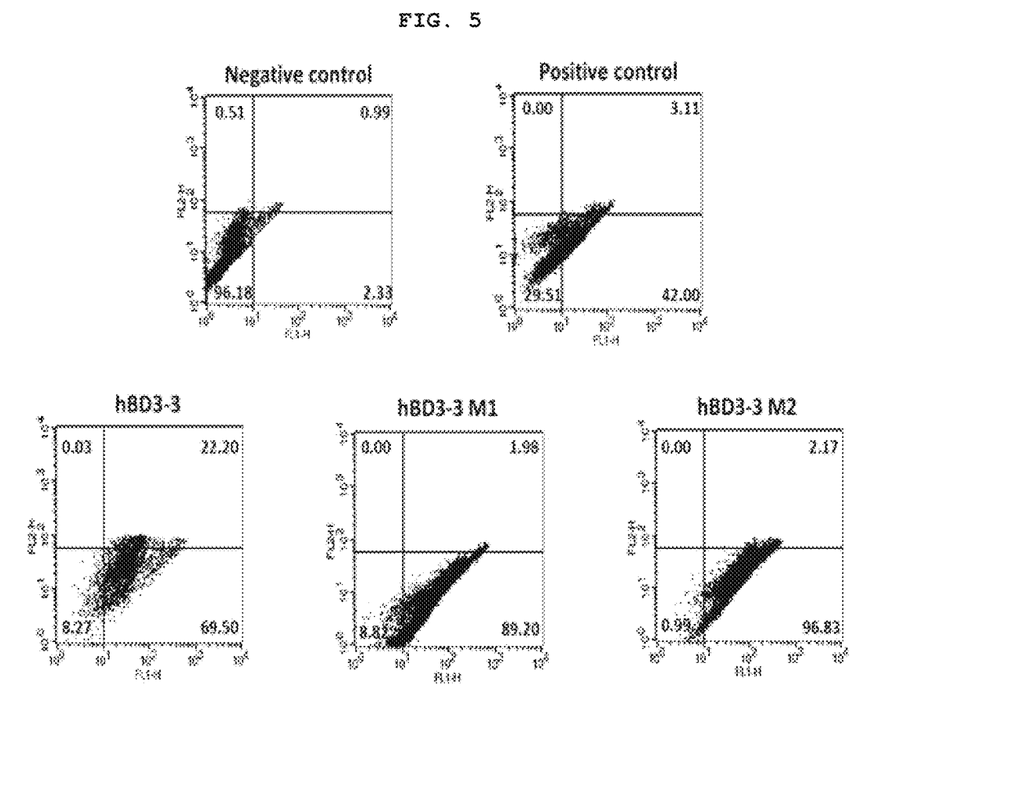
FIG. 5 shows the results of flow cytometry performed to measure apoptosis induced by a cancer stem cell proliferation inhibitory peptide in breast cancer stem cells.

As a result, as shown in FIG. 5, cells positive for annexin V formed 50% of the test group treated with each of the peptides, and this value was significantly higher than that in a negative control group (6.39%). On the contrary, there was no great change in the number of cells in the cell population, which were positive for PI, indicating that the peptides inhibited the growth of the cancer stem cells by transducing a signal that induces apoptosis rather than necrosis.

Example 6: Examination of the Change in Cells by Cancer Stem Cell Proliferation Inhibitory Peptide at Molecular Cellular Level In order to examine the NF-κB-mediated change in cells by the cancer stem cell proliferation inhibitory peptide at the molecular cellular level, $5 \times 10^2$ hBCSCs were seeded in a 10-cm dish, and then cultured in hBCSC complete medium (Celprogen, USA). After 20 hours of culture, the cells were treated with 200 μM of each of the cancer stem cell proliferation inhibitory peptide and the peptides of SEQ ID NO: 1-3 for 2 hours.

Next, in order to compare the expression levels of proteins in the cells, the cells treated with each of the cancer stem cell proliferation inhibitory peptides were treated with RIPA cell extraction reagent (Pierce, USA) according to the manufacturer's instruction to obtain cell lysates. Proteins in the isolated hBCSCs lysates were quantified by Bradford's assay and electrophoresed on 10% polyacrylamide gel at 120 volts for 4 hours. Then, the proteins were transferred to nitrocellulose membranes using transfer buffer (12.5 mM Tris, 0.1M glycine, pH 8.3) at 310 mA for 2 hours. The membranes were blocked with a blocking solution (5% nonfat dry milk, in TBS), and then reacted with primary antibodies (Phosphorylated IκBα (pIκBα), Phosphorylated p65 (pp65); Cell Signaling, USA, N-Cadherin, p16, Fer, Actin; Santa Cluz, USA, Alkaline phosphate (ALP), Phosphorylated Fer (pFer); Abcam, USA), added to the blocking solution to a concentration of 1 μg/ml, at 4° C. overnight. In the morning of the next day, secondary antibody for each of the primary antibodies was added to the blocking solution at a ratio of 1:2000, and the membranes were reacted with the secondary antibodies at room temperature for 1 hour. Next, the membranes were visualized with X-ray film using ECL (enhanced chemo-luminal) in a dark room.

Figure 6:
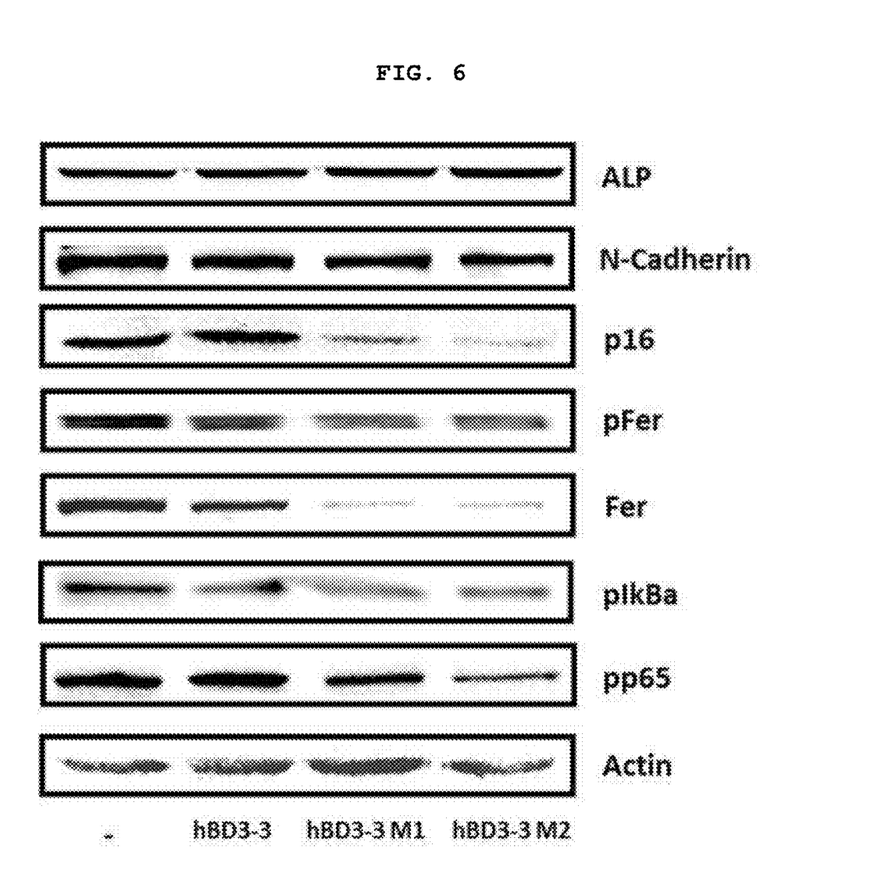
FIG. 6 shows the results of analyzing cell migration and cell proliferation-related proteins by Western blotting in order to examine the change in the proteins by a cancer stem cell proliferation inhibitory peptide in breast cancer stem cells at the molecular level.

As a result, as shown in FIG. 6, when the cells were lysed and the change in protein activities in the cells by treatment with the peptide was examined, it was observed that the peptides of SEQ ID NO: 1-3 inhibited the phosphorylation of IκBα and p65 in the cells, and reduced the expression levels of Fer and pFer in proportion to this inhibition. It is known that Fer belongs to the FPS/FES family and influences cell adhesion and the reconstitution of cytoskeletal protein such as actin. Particularly, it is known that Fer is involved in metastasis by causing a change in the aggressiveness of cancer cells and that as the expression of Fer increases, the aggressiveness of cancer cells also increases. In addition, it was observed that the expression of N-cadherin that is a marker protein of cancer stem cells or aggressive metastatic cancer cells also decreased in the peptide-treated group. This indicates that the peptide inhibits NF-κB among proteins in cancer stem cells and, at the same time, affects the growth mechanism and aggressiveness (metastasis) of cancer stem cells by inducing a change in cell adhesion.

INDUSTRIAL APPLICABILITY

The peptide that inhibits the proliferation of cancer stem cells and induces the apoptosis of such cancer stem cells inhibits the intranuclear movement of NF-κB protein in cancer stem cells to thereby inhibit of growth of cancer stem cells and induce apoptosis of such cells, and thus it can be used as an active ingredient of the anticancer composition.

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof.

The invention claimed is:

1. A method for treating breast cancer, the method comprising:
   administering a peptide to a patient with breast cancer, wherein the peptide is represented by an amino acid sequence of SEQ ID NOs: 2 or 3.

2. The method of claim 1, wherein the peptide inhibits the activity of NF-κB in breast cancer cells or breast cancer stem cells.

3. The method of claim 1, wherein the peptide inhibits the proliferation of breast cancer cells or breast cancer stem cells.

4. The method of claim 1, wherein the peptide induces the apoptosis of breast cancer cells or breast cancer stem cells.

5. The method of claim 2, wherein the breast cancer stem cells are included in breast cancer cells derived from a metastatic breast tumor.

6. The method of claim 1, wherein the administering is by oral, injection, or local transplantation.

7. The method of claim 6, wherein the local transplantation comprises administering a gelling agent that comprises a synthetic polymer or a natural polymer.

8. The method of claim 7, wherein the synthetic polymer is any one selected from the group consisting of polylacticglycolic acid, and poloxamer.

9. The method of claim 7, wherein the natural polymer is any one selected from the group consisting of collagen, chondroitin sulfate, and chitosan.

10. The method of claim 3, wherein the breast cancer stem cells are included in breast cancer cells derived from a metastatic breast tumor.

11. The method of claim 4, wherein the breast cancer stem cells are included in breast cancer cells derived from a metastatic breast tumor.

* * * * *